(12) United States Patent
Gründeman et al.

(10) Patent No.: US 10,070,855 B2
(45) Date of Patent: Sep. 11, 2018

(54) SURGICAL DEVICE FOR PROVIDING ACCESS TO A SURGICAL SITE

(71) Applicant: UMC UTRECHT HOLDING B.V., Utrecht (NL)

(72) Inventors: Paul Frederik Gründeman, Bilthoven (NL); Paul Barteld Kwant, Valkenburg a/d Geul (NL)

(73) Assignee: UMC UTRECHT HOLDING B.V., Utrecht (NL)

( * ) Notice: Subject to any disclaimer, the term of this patent is extended or adjusted under 35 U.S.C. 154(b) by 274 days.

(21) Appl. No.: 14/895,268

(22) PCT Filed: Jun. 12, 2014

(86) PCT No.: PCT/EP2014/062292
§ 371 (c)(1),
(2) Date: Dec. 2, 2015

(87) PCT Pub. No.: WO2014/198855
PCT Pub. Date: Dec. 18, 2014

(65) Prior Publication Data
US 2016/0120531 A1    May 5, 2016

Related U.S. Application Data

(60) Provisional application No. 61/833,938, filed on Jun. 12, 2013.

(51) Int. Cl.
*A61B 1/32* (2006.01)
*A61B 17/02* (2006.01)
(Continued)

(52) U.S. Cl.
CPC ........ *A61B 17/0218* (2013.01); *A61B 5/0422* (2013.01); *A61B 5/6847* (2013.01);
(Continued)

(58) Field of Classification Search
CPC ...... A61B 17/0218; A61B 2017/00557; A61B 2017/0237; A61B 2017/0225;
(Continued)

(56) References Cited

U.S. PATENT DOCUMENTS 3,863,639 A * 2/1975 Kleaveland ........ A61B 17/0293 128/850
4,984,564 A * 1/1991 Yuen .................. A61B 17/0293 600/207

(Continued)

FOREIGN PATENT DOCUMENTS

| WO | 92/21292 A2 | 12/1992 |
| WO | 01/54568 A1 | 8/2001 |
| WO | 2008/042374 A2 | 4/2008 |

*Primary Examiner* — Zade Coley
*Assistant Examiner* — Jessica Weiss
(74) *Attorney, Agent, or Firm* — Richard M. Goldberg

(57) ABSTRACT

A surgical device (5) for application in a treatment performed on the human or animal body (1) with the aim of providing access to a surgical site in the body, includes at least one inflatable chamber (70, 71, 72) which can be inflated from a collapsed state to an expanded state, in which expanded state the device is suitable for exerting a force on an organ or tissue at the surgical site, at least one elongated flexible member (8, 80), which member at its proximal end (801) is operatively connected to the device, and which member has a length to allow the distal end (800) of the member to be fixed to a fixation site (100, 101) outside of the body, and methods of using this device.

19 Claims, 4 Drawing Sheets

(51) Int. Cl.
  *A61B 90/00* (2016.01)
  *A61B 5/00* (2006.01)
  *A61B 5/042* (2006.01)
  *A61B 17/00* (2006.01)
  *A61B 90/30* (2016.01)

(52) U.S. Cl.
  CPC ............ *A61B 5/6865* (2013.01); *A61B 90/02* (2016.02); *A61B 2017/00557* (2013.01); *A61B 2017/0225* (2013.01); *A61B 2017/0237* (2013.01); *A61B 2090/306* (2016.02)

(58) Field of Classification Search
  CPC ............ A61B 2017/0243; A61B 90/02; A61B 5/0422; A61B 5/6847; A61B 5/6865; A61B 2090/306
  USPC .................... 600/207, 204, 210, 235; 606/90
  See application file for complete search history.

(56) References Cited

U.S. PATENT DOCUMENTS

| | | | | |
|---|---|---|---|---|
| 5,295,994 A * | 3/1994 | Bonutti | .............. | A61B 17/0218 604/103 |
| 5,309,896 A * | 5/1994 | Moll | ................ | A61B 17/00234 128/898 |
| 6,080,168 A * | 6/2000 | Levin | ............... | A61B 17/00234 606/108 |
| 9,486,200 B2 * | 11/2016 | Melsheimer | ........ | A61B 17/0218 |
| 2002/0013601 A1 * | 1/2002 | Nobles | ..................... | A61B 1/32 606/193 |
| 2002/0147406 A1 * | 10/2002 | von Segesser | ....... | A61B 5/0422 600/509 |
| 2004/0049099 A1 * | 3/2004 | Ewers | ...................... | A61B 1/32 600/206 |
| 2004/0054353 A1 | 3/2004 | Taylor | | |
| 2006/0293685 A1 * | 12/2006 | Stone | .................... | A61B 17/025 606/90 |
| 2007/0288095 A1 * | 12/2007 | Wirtel | ..................... | A61F 2/441 623/17.16 |
| 2009/0062618 A1 * | 3/2009 | Drew | ................ | A61B 17/0218 600/204 |
| 2009/0137877 A1 * | 5/2009 | Minnelli | ............ | A61B 17/0218 600/204 |
| 2009/0312807 A1 * | 12/2009 | Boudreault | .......... | A61B 17/025 606/86 R |
| 2010/0292718 A1 * | 11/2010 | Sholev | ............. | A61B 17/00234 606/151 |
| 2013/0317303 A1 * | 11/2013 | Deshmukh | ......... | A61B 17/0218 600/202 |

\* cited by examiner

SURGICAL DEVICE FOR PROVIDING ACCESS TO A SURGICAL SITE

GENERAL FIELD OF THE INVENTION

The present invention pertains to a surgical device for application in a treatment performed on the human or animal body with the aim of providing access to a surgical site in said body, the device comprising at least one inflatable chamber which can be inflated (for example using gas or a liquid such as buffered saline solution) from a collapsed state to an expanded state, in which expanded state the device is suitable for exerting a force on an organ or tissue at said surgical site. The invention also pertains to the combination of such a device with a stylet, and to methods for using the device.

BACKGROUND ART

Traditional heart and lung surgery is highly invasive. The chest is cracked widely open for exposure of surgical sites. High quality repair is achieved, but nevertheless considerable procedural related health risks and major discomfort are encountered by about 40% of the patients after open-thoracic surgery. Recently, minimal invasive surgery has gained interest, because it reduces all over operative stress due to less physical trauma and patients are increasingly requiring to be left with fewer scars. However, small incision access cardiothoracic surgery is difficult because the space between the ribs is limiting instrument passage and foremost hypothetical because the breathing lung obstructs free access to e.g. the heart. Alternative approaches in order to expose the heart minimal invasively are one-side lung ventilation or high pressure gas insufflation. The latter method however leads to crunching of the lungs. A more recent approach of minimal invasive surgery is by routing through an inflatable device that in its expanded state exerts forces on one or more organs and tissue to provide access to the site. Such a device is also known as a space maker or spacemaking device.

EP 1 744 678 discloses a device and method as referred to here above in the "General field of the invention" section. This device comprises multiple elongated expansion members which constitute a spatial structure, the elongate members being interconnected at their ends by nodes. The plane between the elongate members is provided with a flexible web to enhance the formation of an open surgical site.

DE 100 40 774 discloses a cylindrical balloon like inflatable device durably attached to a stylet for precisely navigating and positioning of the device in the body. The device has a continuous wall which may be divided into separate chambers, the chambers being in fluid connection. This way an even inflation of the device can be obtained.

U.S. Pat. No. 5,562,603 discloses an inflatable device which is constituted as a closed ball-like object of which the walls are made of a relatively inelastic and tough film of plastic. Any object piercing the wall is sealed immediately around its circumference to keep the expanded form intact.

OBJECT OF THE INVENTION

It is an object of the invention to provide an improved device for providing access to a surgical site in said body, and to provide improved methods of using this device.

SUMMARY OF THE INVENTION

In order to meet the first object of the invention a surgical device according to the GENERAL FIELD OF THE INVENTION has been devised, wherein the device comprises at least one elongated flexible member, which member at its proximal end is operatively connected to the device, and which member has a length to allow the distal end of the member to be fixed to a fixation means outside of the body.

In order to meet the second object of the invention applicant has devised a method for positioning the surgical device in a human or animal body, the method comprising inserting the device in the collapsed state into the body, inflating the at least one chamber to the expanded state such that the device exerts a force on an organ or tissue at said surgical site, guiding the distal end of the flexible member outside of the body, positioning the distal end at a fixation site of a fixation means such that the member is able to spatially position the device, and fixing the distal end at the fixation site to preserve the spatial position of the device.

It was applicants recognition that the known devices lack a means of fixing the device in the body. With the current invention, the device can be positioned in the body, space to provide access to the surgical site can be created and importantly, this space can be reliably maintained. This way, surgical methods can be performed with an improved rate of success.

At the same time applicant has devised a surgical device for application in a treatment performed on the human or animal body with the aim of providing access to a surgical site in said body, the device comprising multiple inflatable chambers which can be inflated to turn the device from a collapsed state into an expanded state, in which expanded state the device is suitable for exerting a force on an organ or tissue at said surgical site, characterised in that the chambers are laterally contiguous thereby forming a wall of the device, wherein two neighbouring chambers, preferably each pair of two neighbouring chambers, are laterally connected at a seam, wherein each of the said two neighbouring chambers convexly bulges towards the seam. This device can be combined (further improved) with any of the features of the embodiments of the invention as outlined below in the section EMBODIMENTS OF THE INVENTION.

Applicant has also devised a combination of a surgical device for application in a treatment performed on the human or animal body with the aim of providing access to a surgical site in said body, the device comprising at least one inflatable chamber which can be inflated from a collapsed state to an expanded state, in which expanded state the device is suitable for exerting a force on an organ or tissue at said surgical site, and a stylet for guiding the device into the body, characterised in that the stylet is removably connected to the device. This combination of the device and a stylet can be combined (further improved) by using for the device, any of the features of the embodiments of the invention as outlined below in the section EMBODIMENTS OF THE INVENTION.

DEFINITIONS

A flexible member is a member that can be flexed to take another shape, but that is elastic such that it can be flexed back to take its original shape.

The proximal and distal ends of an elongated member are the two opposing functional ends of this member. This does not exclude that the member extends beyond the proximal and distal end.

A tether is a cord-like, highly flexible elongated member (such as a rope, line, ribbon, fine chain etc.) that anchors something movable to a reference point, the reference point typically being spatially fixed.

A stylet is a fine surgical rod, which is fairly rigid, but is able to be flexed such that it can form a bend.

A wall is a continuous (closed), in essence two-dimensional structure that can prevent passage of an object, which structure is optionally provided with an opening that can serve as a passage for the object through the wall.

For separate vessels to be in fluid connection means that fluid can freely flow from one vessel to the other when there is a pressure difference. It may be that the pressure difference has to meet a predetermined threshold before the fluid will start to flow, for example to open a restriction or automatic valve.

A sleeve is a tube (which may be conical) extending between two ends, having a continuous endless wall between these ends, and at least one opening at one of the ends which opening corresponds to the inner diameter of the tube. Typically the other end also has an opening that corresponds to the inner diameter of the tube.

Embodiments of The Invention

In a first embodiment the elongated flexible member is a tether. A tether has the advantage that it may be very flexible and yet strong. This way, it can be used in a very versatile way to fix the position of the device using a fixation means outside of the body, for example by fixing the distal end to the skin of the patient, a fixing means such as a table frame or a flexible fixture attached to that frame (see for example the flexible arm of an Octopus™ Stabilizer (see U.S. Pat. No. 6,464,629; available from Medtronic Inc.), or any other means. A tether could also be used to fix the device to an internal part of the body of the patient. The latter option may be used in particular when the device comprises two or three tethers, such that there is an additional tether available for fixation to a fixation site outside of the patient's body.

In an alternative embodiment the elongated flexible member is a stylet. A stylet is less flexible than a tether but has the advantage over a tether that it can be used in the stages before fixation the device, viz. the positioning (navigation) of the device and the creation of the space (for example by exerting forces on an organ to push the organ aside). The stylet may then be fixed with its distal end to a fixation site outside of the patient's body. In a further embodiment this stylet is removably connected to the device. This way, if the less flexible stylet is in one way or the other obstructing the passageway for instruments, or otherwise may negatively influence the surgical procedure, it can be removed after the device is positioned.

Preferably the device comprises in combination one removably connected stylet (although two or more stylets may also be advantageously used) and two or three tethers.

In yet another embodiment the device comprises at least one wall, the wall comprising multiple inflatable chambers which are in fluid connection. The presence of an inflatable wall, as opposed to the device being a closed "balloon-like" constitution (such as known from U.S. Pat. No. 5,562,603) has the advantage that the device may have fenestrations or other openings, and still be inflated to reach its expanded state. In a further embodiment the chambers of the wall are laterally contiguous, wherein two neighbouring chambers are laterally connected at a seam, wherein each of the two neighbouring chambers convexly bulges towards the seam (such that the wall attains a "Chesterfield-like" surface). Applicant found that this way a very stable wall may be created which is ideally suitable for use in surgical methods, with a limited risk of damaging surrounding tissue and organs.

In a further embodiment of this "Chesterfield" embodiment the wall is formed as a sheeting comprising two opposing layers of deformable (but preferably tough, hardly stretchable) material, the sheeting comprising the multiple chambers connected at the seam, the seam being formed according to a predetermined pattern by having a connection of the two opposite layers at the seam. This appears to be a convenient way of making the device. The layers can be attached at the seam by gluing, welding or any other technique that does not leave permanent perforations. Preferably the sheeting comprises a third layer interposed between the two opposing layers. This way, separate chambers are created at opposing sites of the wall. This reduces the risk of the device deflating when a chamber gets pierced. In an embodiment the wall comprises multiple chambers in two perpendicular directions. This provides a very good stability of the device in expanded state. In another embodiment the wall is formed as an endless sleeve, thus leaving one or two large openings at the ends of the device.

In another embodiment of the "Chesterfield" embodiment, the chambers are part of one continuous tube, which tube is rolled up to form multiple windings, each winding representing a chamber. This way, different forms can be created easily, while maintaining the convex bulges of the chambers towards the seam. In a further embodiment the windings form a cone. This embodiment appears to be ideally suitable for creating space around the heart. Preferably the bottom winding of the cone is flexed away from the cone to form a lateral entrance towards the interior of the cone.

The above embodiments can be further altered by having the wall comprising a second set of multiple inflatable chambers which are in fluid connection, the chambers of the second set not being in fluid connection with the chambers of the first set. In particular, by having two or more sets of chambers that are in fluid connection, the device can be expanded in different stages, for example allowing telescopic expansion, or the device can be inflated to create different forms that allow a match with the requirements of an operation or even the different stages of the operation.

Further embodiments are described in the appended claims. All the above mentioned embodiments can be used in combination with the methods according to the invention.

BRIEF DESCRIPTION OF THE DRAWINGS

The invention will now be further explained using the following figures and examples.

EXAMPLES

Figure 1:
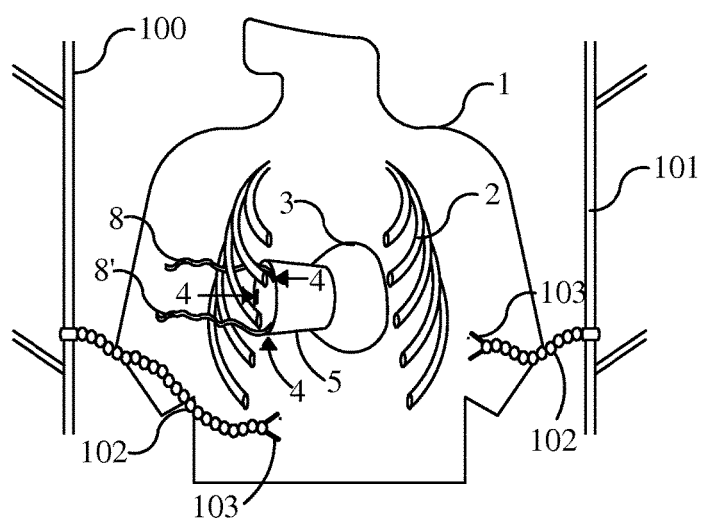

FIG. 1 schematically shows a surgical device according to the invention placed into a human body.

Figure 2:
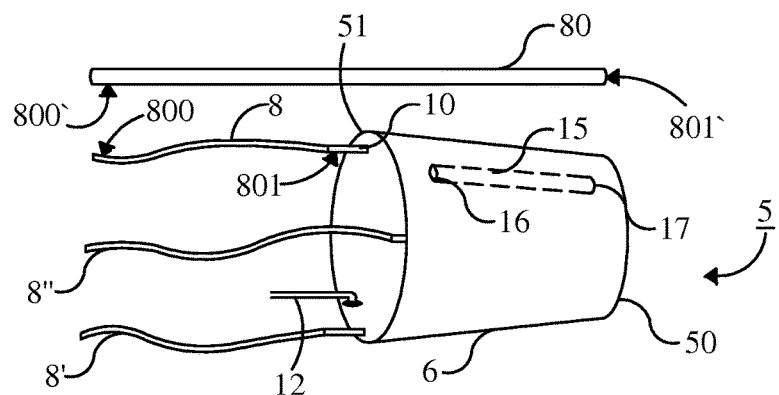

FIG. 2 schematically shows a device according to the invention.

FIG. 3 schematically shows various walls for an inflatable device suitable for providing access to a surgical site in a body.

Figure 4:
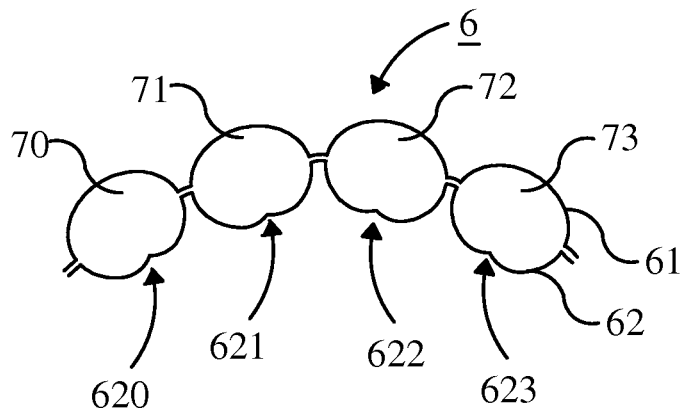

FIG. 4 schematically shows a preferred wall for a device according to the invention when under bending stress.

Figure 5:
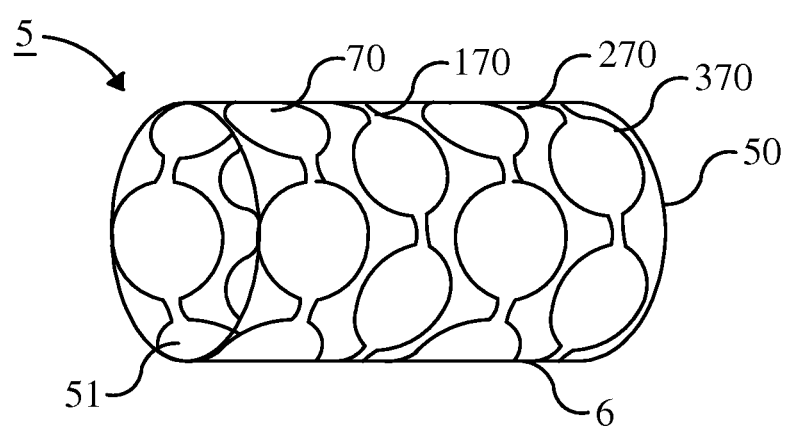

FIG. 5 schematically shows the main part a device according to another embodiment of the invention.

Figure 6:
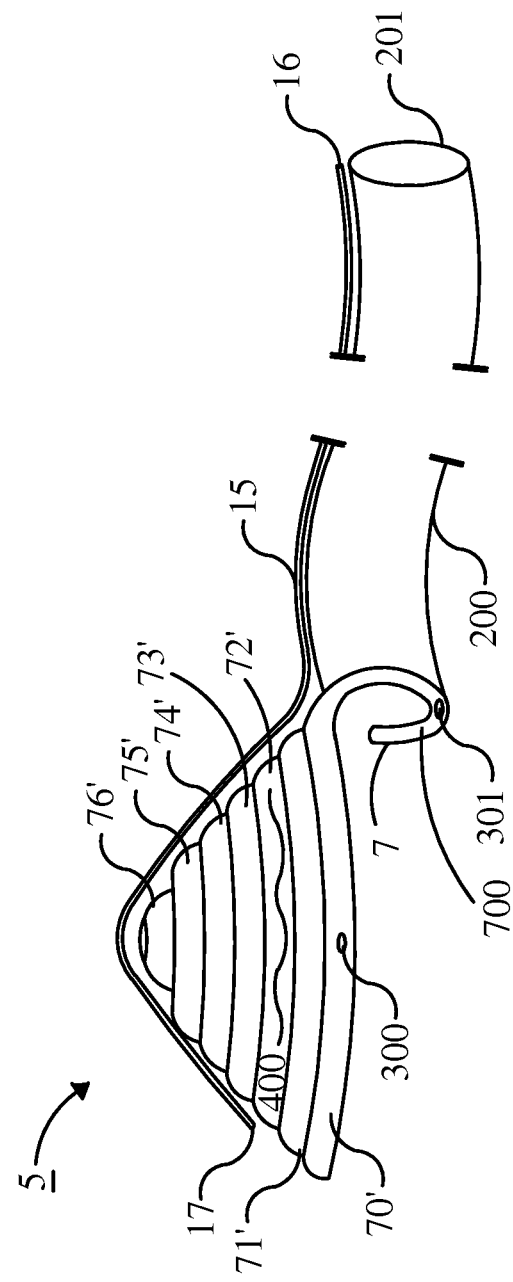

FIG. 6 schematically shows another embodiment of a device according to the invention.

Example 1 describes the use of a device according to the invention.

Example 2 describes the use of another device according to the invention.

DETAILED DESCRIPTION

FIG. 1

FIG. 1 schematically shows a surgical device according to the invention placed into a human body 1, showing part of the ribs 2 and the heart 3. The figure shows the device 5 in expanded state, inserted into the body via one of the incisions 4. The device is positioned with an open top end against the heart. The device is provided with three tethers (8, 8'; only two are shown in FIG. 1) that can be used to stably fix the device to a fixation site outside the body in order to maintain its position in the body. For this, use can be made of the table frame 100 and 101, to which frame flexible arms 102 are slidably attached. The configuration of these arms can be fixed such that they maintain their 3D shape. Such arms are for example described in U.S. Pat. No. 6,464,629 and are for example used in the Octopus™ device as available from Medtronic Inc. The distal ends of the tethers can be fixed to these arms using the mechanical beak 103. This way the space making device 5 can be stable maintained at its preferred position. Another way of fixing the tethers to the outside of the body is by simply fixing the tethers to the skin of the patient.

FIG. 2

FIG. 2 schematically shows the spacemaking device 5 as depicted in FIG. 1, but now in greater detail. The device is shaped as a slightly conical sleeve, with a closed wall 6 and two large openings at its ends 50 and 51. The wall in this embodiment comprises multiple inflatable chambers (which are not visible in FIG. 2) which are in fluid connection. Three tethers 8, 8° and 8" are durably attached to the inside side of the wall 6 using fixing strips 10. The wall can be inflated (typically using a saline solution) via vent tube 12. In this embodiment, the device comprises a narrow sub-sleeve 15, having an opening 16 and a dead end 17. This sleeve can accommodate stylet 80, which may be slided into the sleeve 15 until its proximal end 801' reaches dead end 17. This way, the stylet can be used to push the device into the body (when collapsed), navigate the device to the surgical site, and optionally create space by exerting a force on surrounding tissue or organs. The length of the stylet 80 is such that even after positioning of the device in the body, the distal end 800' is situated outside of the body such that it can be easily grasped, for example for removal of the stylet by retracting the stylet out of the sleeve 15, or for fixing the stylet to an external fixature such as the arm 102 (see FIG. 1). It is understood that the stylet can be connected to the device in any other suitable way, and also that two or more stylets are used that are in operative, preferably removable, connection with the device.

FIG. 3

Figure 3A:
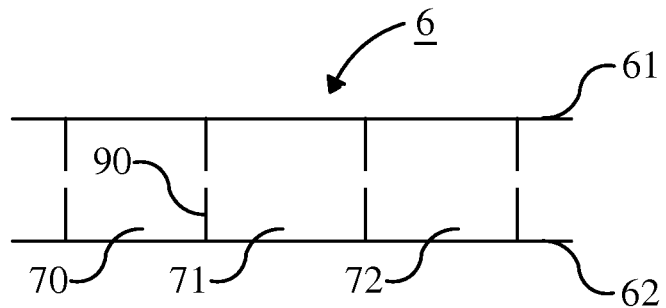

FIG. 3, composed of sub-FIGS. 3A through 3D, schematically shows various walls, at least a part thereof and in an expanded state, for an inflatable device suitable for providing access to a surgical site in a body. The wall 6 of FIG. 3A is a wall as known from DE 100 40 774. This wall comprises contiguous chambers 70, 71 and 72 which have a lateral common boundary in the form a lamella 90, each lamella being provided with a hole to make sure that the chambers are in fluid connection.

Figure 3B:
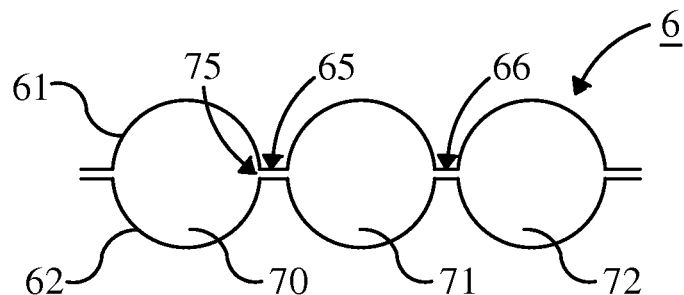

In FIG. 3B a wall 6 according to a specific embodiment of the present invention is depicted, this embodiment being referred to here above as a "Chesterfield" embodiment. In this embodiment the wall 6 wall is formed as a sheeting comprising two opposing layers 61 and 62. These layers are made of a deformable material, the sheeting comprising multiple chambers 70, 71 and 72 connected at seams 65 and 66 respectively. These seams are formed by welding the sheets together according to a predetermined pattern. Vents 75 are present to fluidly connect the chambers. By configuring the two opposing sheets this way, the chambers are laterally contiguous. This way, two neighbouring chambers are laterally connected at the seam and each of the two neighbouring chambers convexly bulges towards the seam.

Figure 3C:
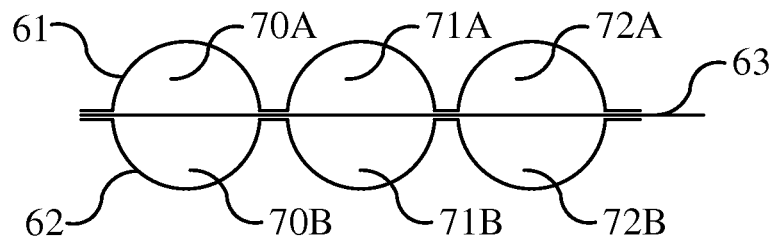
Figure 3D:
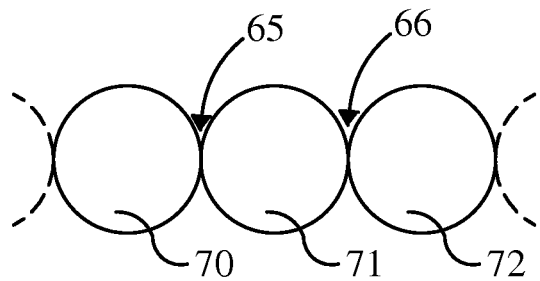

Other embodiments of this Chesterfield embodiment are depicted in FIGS. 3C and 3D. In FIG. 3C an embodiment is shown that corresponds to the embodiment of FIG. 3B, albeit that the sheeting comprises a third layer 63 interposed between the two opposing layers. This way, chambers 70A, 71A and 72A form a first set of chambers and chambers 70B, 71B and 72B form a second set of chambers. Both sets are inflated separately.

FIG. 3D shows another example of the Chesterfield embodiment, wherein the chambers 70, 71 and 72 are part of one continuous tube, which tube is rolled up to form multiple windings (700, 70', 71', 72', 73', 74', 75', 76'; see FIG. 6), each winding representing a chamber. Also in this particular, two neighbouring chambers are laterally connected at a seam (65, 66), for example by gluing, and each of the two neighbouring chambers convexly bulges towards the seam.

FIG. 4

FIG. 4 schematically shows a preferred wall 6 for a device according to the invention when under bending stress. The depicted wall 6 is a wall according to the Chesterfield embodiment, in this case the same embodiment as the one depicted in FIG. 3B, thus being constituted as a sheeting comprising two opposite layers 61 and 62, having seams to provide separate chambers 70, 71, 72 and 73. As depicted the wall 6 is bent, which leads to buckles 620, 621, 622 and 623 respectively. The result is that there are counter forces that try to bend the sheeting back to a flat shape. This in the end results in a rigid (form stable) expanded structure, in particular when applied in this circular shape.

FIG. 5

FIG. 5 schematically shows the main part a device 5 according to another embodiment of the invention, corresponding to the embodiment of FIG. 2. For reasons of clarity, the device is depicted in an unfolded but not yet inflated configuration (the chambers are not yet filled with medium), and the tethers, stylet sleeve and vents for inflating and deflating are not shown. In this embodiment the wall 6 is constituted as a tube having openings at its ends 50 and 51. The wall has a Chesterfield structure as explained in conjunction with FIGS. 3B and 4. As depicted the wall comprises a first set of chambers 70 and 170, all chambers in this set being in fluid connection, and a second set of chambers 270 and 370 which are also in fluid connection. Both sets can be inflated and deflated independently. This means that the device can be expanded and collapsed telescopically.

FIG. 6

FIG. 6 schematically shows another embodiment of a device 5 according to the invention. This embodiment of the device 5 is basically comprised of one continuous tube 7, which tube is rolled up to form multiple spiral windings (700, 70', 71 ', 72', 73', 74', 75', 76'), each winding representing a chamber in the sense of the present invention. The windings are laterally connected by welding the surface of the tube windings. In this embodiment the windings form a cone, having an open bottom and a small opening at the top. The cone has a height of about 5 cm and a base width of 6-10 cm. The device is provided with a conduit 200 of about 5 cm in diameter (for the scoop and surgical tool) and a length of about 16-20 cm. The entry side 201 of this conduit (after positioning of the device in the body) is outside the body. At the exit side the sleeve is connected with tube winding 700 of continuous tube 7. This winding 700 is the last part of the spiral cone and is flexed away from the lowest winding 70' of the cone. A sleeve 15 having a diameter of 5 mm is glued to the entire exterior aspect of the spiral dome shape, over the top of the cone and over the conduit 200. This sleeve 15, having its entrance 16 outside of the body, serves as an guiding for the stylet (not shown) that is in place for navigating, manipulating and fixation of the device and has a blind end 17 as explained before in conjunction with FIG. 2. The device is optionally provided with one or more tethers for additional fixation of the device at the surgical site. The device is provided with electrodes 300 and 301 for making an electrocardiogram. Further provided are multiple luminescent fibres 400, one of which is shown on the outside of the cone, the others being present on the inside to illuminate the heart. The vent for inflating the device, which vent in essence runs along sleeve 15, is not shown. In deflated (collapsed) condition this device can be fed through a 10-12 mm trocard. In an alternative embodiment, the cone is formed with two or more separate tubes (not being in fluid connection) which are concurrently or consecutively wound to form the cone.

Example 1

A spacemaking device according to FIG. 5 (with the Chesterfield configuration) has been designed, manufactured and tested. The device has three tethers corresponding to the device as shown in FIG. 2, and is made of a tough but flexible biocompatible material (as known in the art). In this example the device was created by fixing together two sheets of thin walled poly-urethane. Efficacy of the device was tested in the porcine model with the hypothesis that the device would facilitate minimally invasive cardiothoracic surgery without the need of lung separation techniques or carbon dioxide overpressure insufflation. The device was applied in the chest of (at least) 7 anesthetized pigs (90-100 kg) placed on standard endotracheal ventilation. The size of the device was adjusted to the chest size of the animal and the distance from the chest wall to the heart. Packed in deflated (collapsed) condition, the device was introduced into the right or the left chest, via a 3 cm-incision in the fifth intercostal space and positioned anteriorly of the lung lobes prior to expansion. Introduction appeared to be easy and unhindered. The device was inflated up to 0.6 bar thereby pushing the lung tissue gently away cranially (direction of head), posteriorly (to the back) and caudally (to the tale).

Two 10 mm trocar-ports (key-hole tubes) were consecutively introduced in the 4th and 7th intercostal space posteriorly to the anterior axillary line to be used as instrumental ports and thereafter, once the device was positioned, as a guide to lead out the tethers. The loose ends of the tethers were brought outside the body by picking those with a grasper and fixed to the skin of the patient or draping towels. In this way the device was towed to the chest wall thus preventing migration of the entry side of the tunnel. Trocars were positioned with entry side outside the body and exit side inside the body encompassed by the device. The spacemaking device created an oval shaped tunnel sizing roughly 5×10 cm allowing unhindered feeding and maneuvering of thoracoscopic instruments. Thus, any instrument passing a trocard lumen was exclusively guided to the space (a tunnel) created by the device. A stylet was introduced which, after introduction into a sleeve (see ref. 15 in FIG. 2) with a blind ending positioned at the far side of the device, was functional for maneuvering, (re)positioning and pushing tissue junxtional to the device aside (e.g. tissue like diaphragm or pericardial sac). Occasionally, the stylet was additionally connected to an external fixation arm (see ref. 102 in FIG. 1) thus holding tissue inside the body away in order to maintain the position of the device. Placement and stable positioning concurred without interference with pulmonary function or respiratory compromise. In addition, no animal experienced serious circulatory (hemodynamic) deterioration throughout the experiments. Alternatively, the device was introduced in the pericardial space through the subxiphoid access, depending on the intended (surgical) procedure on the heart to be performed. In the pericardium, the device encompassed the entire heart and was capable to push the pericardium aside thus exposing exterior aspects of the heart. Alternatively, the device was placed in deflated condition between the heart and surrounding pericardial sac. Inflated, the device provided an oval shaped tunnel from skin to heart tissue allowing feed of instruments toward external structures of the heart such as the heart appendages for removal, clamping or ablation of tissue.

Different closed-chest surgical procedures such as valve surgery e.g. on the mitral valve, arrhythmia surgery like left atrial appendage exclusion and pulmonary vein exposure for ablation, epicardial pacemaker lead placement, stem cell injection for cardiac regenerative therapies on a mechanically stabilized heart and endoscopic stabilization for coronary surgery were successfully performed. Alternatively, in inflated condition, the device functioned as a wound retractor in open thoracic operations. Complete removal of the embodiment was unhindered and fast through one body opening by pulling on one tether attached to the embodiment. Inspection of exposed ventilated lung tissue which was all time in contact with the device showed normal physical aspects without remnant atelectasis (undeployed non-ventilated territories). Based on these results, it is expected that the spacemaking device will be successful in other fields as well, such as laparoscopy, prostatectomy, neurosurgery, spine surgery and gynaecology.

Example 2

In this example the use of a device according to the embodiment of FIG. 6 is described. FIG. 6 schematically depicts an embodiment that can be specifically used to create the necessary space for an exclusion procedure of the left atrial appendage of the human heart. The left atrial appendage (LAA) is considered to be a focus of malign cardiac arrhythmia's. The access to the anatomical structure which is nicknamed the left heart ear (look alike) is the pericardial space. The entry port is made just below the sternal bone, at the site of the xiphoid process. Through the conduit 200 of about 20 cm between the left heart chamber and the pericardial sac the surgeon can feed a flexible scoop and an ablation or exclusion tool. One goes behind the heart. The atrial appendage is situated about 3 cm left from the sternal bone in the frontal plane but some 10 cm back to the spine and in the horizontal plane at the level of the 5th intercostal space. The LAA arises from the heart from its base 4-6 cm and with a variable height of about 4-6 cm.

The tubes can be inflated with air but preferentially with saline under high pressure. The vent for this saline follows in essence the same route as the sleeve 15 for the stylet but ends at the top of the cone connected with the beginning of the tube 7. At the other end of this vent, outside the body, a luer lock stopcock is in place.

The invention claimed is:

1. A method for positioning a surgical device in a human or animal body, the surgical device being suitable for application in a treatment performed on the human or animal body with an aim of providing access to a surgical site in the body, the surgical device comprising:
   at least one inflatable chamber configured to be inflated from a collapsed state to an expanded state, wherein the at least one inflatable chamber comprises at least one wall, the at least one wall forming a first set of multiple inflatable chambers of the at least one inflatable chamber, which are in fluid connection, the chambers formed by the at least one wall are laterally contiguous, two neighboring chambers are laterally connected at a seam and each of the two neighboring chambers convexly bulges towards the seam, wherein the at least one wall is formed as a sheeting comprising two opposing layers of deformable material, the sheeting forming the multiple inflatable chambers connected at the seam, the seam being formed according to a predetermined pattern by having a connection of the two opposite layers at the seam, wherein the sheeting comprises a third layer interposed between the two opposing layers, and
   at least one elongated flexible member, each elongated flexible member having a proximal end operatively connected to the surgical device, the method comprising the steps of:
   inserting the surgical device in the collapsed state into the body,
   inflating the at least one inflatable chamber to the expanded state such that the surgical device exerts a force on an organ or tissue at said surgical site,
   guiding a distal end of the at least one elongated flexible member outside of the body,
   positioning the distal end at a fixation site such that the at least one elongated flexible member is adapted to position the surgical device, and
   fixing the distal end at the fixation site to fix the position of the surgical device.

2. A method according to claim 1, wherein the at least one elongated flexible member comprises at least one tether.

3. A method according to claim 2, wherein the at least one tether comprises at least two tethers.

4. A method according to claim 1, wherein the at least one elongated flexible member is a stylet.

5. A method according to claim 4, wherein the stylet is removably connected to the surgical device.

6. A method according to claim 1, wherein the at least one elongated flexible member comprises one removably connected stylet and at least two tethers.

7. A method according to claim 1, wherein the first set of multiple inflatable chambers are formed in two perpendicular directions with respect to each other.

8. A method according to claim 1, wherein the at least one wall is formed as a sleeve.

9. A method according to claim 1, wherein the at least one wall forms a second set of multiple inflatable chambers of the at least one inflatable chamber which are in fluid connection, the chambers of the second set not being in fluid connection with the first set of multiple inflatable chambers of the at least one inflatable chamber.

10. A method according to claim 1 further comprising at least one conduit to guide instruments to the surgical device.

11. A method for positioning a surgical device in a human or animal body, the surgical device being suitable for application in a treatment performed on the human or animal body with an aim of providing access to a surgical site in the body, the surgical device comprising:
   at least one inflatable chamber configured to be inflated from a collapsed state to an expanded state, and
   at least one elongated flexible member, each elongated flexible member having a proximal end operatively connected to the surgical device, the method comprising the steps of:
   inserting the surgical device in the collapsed state into the body,
   inflating the at least one inflatable chamber to the expanded state such that the surgical device exerts a force on an organ or tissue at said surgical site,
   guiding a distal end of the at least one elongated flexible member outside of the body,
   positioning the distal end at a fixation site such that the at least one elongated flexible member is adapted to position the surgical device, and
   fixing the distal end at the fixation site to fix the position of the surgical device,
   wherein the at least one inflatable chamber comprises at least one wall, the at least one wall forming a first set of multiple inflatable chambers of the at least one inflatable chamber, which are in fluid connection,
   wherein the first set of multiple inflatable chambers formed by the at least one wall are laterally contiguous,
   wherein two neighboring chambers are laterally connected at a seam,
   wherein each of the two neighboring chambers convexly bulges towards the seam,
   wherein the first set of multiple inflatable chambers are part of one continuous tube rolled up to form multiple windings, each winding representing a chamber.

12. A method according to claim 11 further comprising electrocardiogram electrodes:
   on the at least one inflatable chamber, or
   in the at least one inflatable chamber.

13. A method according to claim 11 further comprising a luminescent fiber:
   on the at least one inflatable chamber, or
   in the at least one inflatable chamber.

14. A method according to claim 11, wherein the at least one elongated flexible member comprises at least one tether.

15. A method according to claim 14, wherein the at least one tether comprises at least two tethers.

16. A method for positioning a surgical device in a human or animal body, the surgical device being suitable for application in a treatment performed on the human or animal body with an aim of providing access to a surgical site in the body, the surgical device comprising:
   at least one inflatable chamber configured to be inflated from a collapsed state to an expanded state, wherein the at least one inflatable chamber comprises at least one wall, the at least one wall forming a first set of multiple inflatable chambers of the at least one inflatable chamber, which are in fluid connection, the chambers formed by the at least one wall are laterally contiguous, two neighboring chambers are laterally connected at a seam and each of the two neighboring chambers convexly bulges towards the seam, wherein the inflatable chambers are part of one continuous tube rolled up to form the surgical device into multiple windings, each winding representing a chamber, wherein the windings form a cone, and at least one elongated flexible member, each elongated flexible member having a proximal end operatively connected to the surgical device, the method comprising the steps of:

inserting the surgical device in the collapsed state into the body, inflating the at least one inflatable chamber to the expanded state such that the surgical device exerts a force on an organ or tissue at said surgical site, guiding a distal end of the at least one elongated flexible member outside of the body, positioning the distal end at a fixation site such that the at least one elongated flexible member is adapted to position the surgical device, and fixing the distal end at the fixation site to fix the position of the surgical device.

17. A method according to claim 16, wherein a bottom one of the windings of the cone is flexed outwardly from the cone to form a lateral entrance leading towards an interior of the cone.

18. A method according to claim 16, wherein the at least one elongated flexible member comprises at least one tether.

19. A method according to claim 18, wherein the at least one tether comprises at least two tethers.

\* \* \* \* \*